United States Patent
Li et al.

(10) Patent No.: US 11,649,479 B2
(45) Date of Patent: May 16, 2023

(54) METHODS AND KITS TO DETECT VIRAL PARTICLE HETEROGENEITY

(71) Applicant: LIFE TECHNOLOGIES CORPORATION, Carlsbad, CA (US)

(72) Inventors: Yixin Li, Redwood City, CA (US);
Bharti Solanki, Antioch, CA (US);
Sheung-Mei Shih, Fremont, CA (US);
Peter Bell, Tucson, AZ (US); Darick Dayne, Granite Bay, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 66 days.

(21) Appl. No.: 17/040,250

(22) PCT Filed: Mar. 22, 2019

(86) PCT No.: PCT/US2019/023728
§ 371 (c)(1),
(2) Date: Sep. 22, 2020

(87) PCT Pub. No.: WO2019/183579
PCT Pub. Date: Sep. 26, 2019

(65) Prior Publication Data
US 2021/0017608 A1 Jan. 21, 2021

Related U.S. Application Data

(60) Provisional application No. 62/647,564, filed on Mar. 23, 2018.

(51) Int. Cl.
| | | |
|---|---|---|
| C12Q 1/70 | (2006.01) | |
| C12Q 1/686 | (2018.01) | |
| C12Q 1/68 | (2018.01) | |
| C12N 15/86 | (2006.01) | |

(52) U.S. Cl.
CPC .............. *C12Q 1/68* (2013.01); *C12Q 1/686* (2013.01); *C12Q 1/70* (2013.01); *C12N 15/86* (2013.01); *C12Q 2531/125* (2013.01)

(58) Field of Classification Search
None
See application file for complete search history.

(56) References Cited

U.S. PATENT DOCUMENTS

2014/0242671 A1  8/2014  Grieger et al.

FOREIGN PATENT DOCUMENTS

| WO | WO-2004099423 A1 * | 11/2004 | ........... C07K 14/005 |
|---|---|---|---|
| WO | WO-2007054515 A1 | 5/2007 | |
| WO | WO-2016206807 A1 | 12/2016 | |

OTHER PUBLICATIONS

Nordengrahn, Evaluation of a novel proximity ligation assay for the sensitive and rapid detection of foot-and-mouth disease virus, Veterinary Microbiology, 127, 227-236, 2008. (Year: 2008).*
Rayaprolu, Comparative Analysis of Adeno-Associated Virus Capsid Stability and Dynamics, Journal of Virology, 87(24): 13150-13160, 2013. (Year: 2013).*
Shaw, Implementation of a one-step real-time RT-PCR protocol for diagnosis of foot-and-mouth disease, Journal of Virological Methods, 143(1): 81-85, 2007. (Year: 2007).*
Sommer, Quantification of Adeno-Associated Virus Particles and Empty Capsids by Optical Density Measurement, Molecular Therapy, 7(1): 122-128, 2003. (Year: 2003).*
International Search Report and Written Opinion for Application No. PCT/US2019/023728, dated May 28, 2019, 18 pages.
Schlingemann J, et al., "Novel means of viral antigen identification: improved detection of avian influenza viruses by proximity ligation", Journal of Virological Methods, Elsevier, XP026788553, vol. 163, No. 1, Jan. 1, 2010 (Jan. 1, 2010), pp. 116-122.

* cited by examiner

*Primary Examiner* — Angela M. Bertagna
*Assistant Examiner* — Carolyn L Greene

(57) ABSTRACT

Provided herein are compositions, methods and uses that relate to an easy, accurate and reliable dual or duplex assay that determines both protein and nucleic acid amounts in a viral preparation in a single container and further determines full versus empty virion content.

17 Claims, 7 Drawing Sheets

METHODS AND KITS TO DETECT VIRAL PARTICLE HETEROGENEITY

CROSS-REFERENCE

This application is a United States National Stage Application under 35 USC 371 of International Application No. PCT/US2019/023728 filed on 22 Mar. 2019, which claims the benefit under 35 U.S.C. § 119(e) of U.S. Provisional Application No. 62/647,564, filed 23 Mar. 2018, the entire contents of which are incorporated by reference herein.

FIELD OF THE INVENTION

The present disclosure relates to an efficient, accurate and reliable method to determine both protein and nucleic acid amounts in a viral preparation in a single, dual assay.

BRIEF SUMMARY OF THE INVENTION

Several applications, for example, gene therapy, require that the qualitative and/or quantity attributes of viral preparations be characterized before administration to a subject. The potency of a viral preparation consist of two parts: 1) the ability of viral capsid to transduce cells and 2) the ability of DNA in virus to produce the desired product. Inoperable capsids (for e.g., empty) do not effectively transduce the cells. Thus, an accurate tool to measure the dose and ultimately the potency of viral preparations, and to monitor gene therapy vector quality and potency is therefore needed. Previously, the evaluating step for determining the percentage or ratio of full:empty viral capsids have been by cryogenic transmission electron microscopy (CryoTEM), negative staining TEM, capillary electrophoresis, analytical ultracentrifugation, native agarose gel, alkaline agarose gel, southern blot, dot-blot hybridization, UV spectrophotometry, weak anion exchange chromatography, or mass spectrometry. These techniques are extremely slow, tedious, are capital intensive, require large samples of high purity, and high levels of user training and expertise.

Here we describe a dual/duplex assay that is designed to enable the simultaneous quantitation of vector DNA by quantitative TaqMan assay and viral capsid protein determination by proximity ligation assay (PLA). Both protein and DNA can be quantitated at the same time. The optimized PLA procedure allows the detection of viral proteins in a sensitive manner. Measuring the capsid protein and DNA together leads to the simple, fast, and direct determination of a virus full and empty ratio with a time-to-result of about 4 hours. To validate this approach, we used the Adeno-Associated Virus (AAV) which is a commonly used vector of choice in many gene therapies. In a preferred embodiment, the assay is particularly useful to measure AAV viral full:empty analytics. This novel approach represents a paradigm shift for AAV, and enables the end-user to accelerate their work by obtaining vital information about vector samples with speed, ease, and accuracy.

TaqMan® Protein Assays are an adapted form of PLAT™, a proximity ligation assay technology that combines antibody-protein binding with detection of the reporter nucleic acid by real-time PCR. It has been employed for sensitive and specific measurement of protein/protein expression. Here, in a first step, we use an adapted form of the PLA™ technology to obtain a sensitive and specific measurement of viral protein in a capsid and subsequently, by disassembling the viral capsid, in the second step, we release the viral DNA and accurately measure viral DNA by quantitative PCR (qPCR). The measurement is possible in a single assay, in a single container, in about 4 hours manually, and can be adapted to semi-automated or fully automated methods as well.

In one embodiment, the disclosure provides a method of quantifying a dose of a viral preparation, comprising:
  a) quantifying a total number of viral capsids in the viral preparation via a viral-specific PLA assay;
  b) heating the virus preparation to enable disassembly of the viral capsid, and releasing the viral DNA;
  c) quantifying the total number of viral DNA in the viral preparation via a viral DNA-specific quantitative PCR assay.

In another embodiment, the disclosure provides the method as described above, wherein the quantification in a) for viral capsid and in c) for viral DNA is determined from a reference standard curve, or, wherein the quantification in a) for viral capsid and in c) for viral DNA is determined by digital PCR.

In another embodiment, the disclosure provides the method of any of the claims described above, wherein the viral preparation is selected from the group consisting of parvovirus, adeno-associated virus (AAV), adenovirus, lentivirus, retrovirus, herpesvirus, poxvirus, paramyxovirus, baculovirus, reovirus, alphavirus, flavivirus, and combinations thereof.

In another embodiment, the disclosure provides the method of any of the above claims, wherein the steps a) through c) are all performed in a single container.

In one embodiment, the disclosure provides the method of any of the above claims, wherein the heating of step b) is at least at 80° C.

In another embodiment, the disclosure provides the method of any of the above claims, wherein the heating of step b) is up to 100° C.

In another embodiment, the disclosure provides the method of any of the above claims, wherein the method of quantifying viral protein and viral DNA is done within about 4 hours.

In another embodiment, the disclosure provides the method of any of the above claims, wherein the viral preparation comprises one or more of full genome-containing virus particles, partial genome-containing virus particles, self-complementary genome-containing virus particle (double stranded genome), and genome-free virus particles.

In another embodiment, the disclosure provides the method of any of the above claims, further comprising evaluating a percentage or ratio of full versus empty (full:empty) capsids in the viral preparation.

In another embodiment, the disclosure provides the method of any one of the above claims, wherein the percentage of full viral capsids is from about 1% to about 100%.

In another embodiment, the disclosure provides the method of any one of the above claims, wherein the percentage of full viral capsids is about 60%-100%.

In an embodiment, the disclosure provides a method of measuring the concentration of full AAV capsids in an AAV preparation, comprising:
  a) quantifying a total number of AAV capsids in the AAV preparation via an AAV-specific PLA assay;
  b) heating the AAV preparation to enable disassembly of the AAV capsid, and releasing the AAV DNA;
  c) quantifying the total number of AAV DNA in the AAV preparation via an AAV DNA-specific quantitative PCR assay; and,
  d) evaluating a percentage of full versus empty AAV capsids in the AAV preparation by calculating the ratio of AAV DNA quantity/AAV capsid quantity.

In another embodiment, the disclosure provides the method of the claim above, wherein the quantification in a) for AAV capsid and in c) for AAV DNA is determined from a reference standard curve, or, wherein, the quantification in a) for AAV capsid and in c) for AAV DNA is determined by digital PCR.

In another embodiment, the disclosure provides the method of above claims, wherein the PLA assay is capable of detecting one or more of thirteen serotypes of the AAV capsid antigen.

In another embodiment, the disclosure provides the method of any of claims above, wherein the steps a) through c) are all performed in a single container.

In another embodiment, the disclosure provides the method of any one of the claims above, further comprising evaluating a percentage or ratio of full versus empty (full: empty) AAV capsids in the AAV preparation.

In some embodiments, the disclosure provides the method of any one of the claims above, wherein the percentage of full AAV capsids is from about 1% to about 100%.

In another embodiment, the disclosure provides the method of any one of the claims above, wherein at least 60-100% of the AAV capsids are full AAV capsids.

In some embodiments, the disclosure provides the method of any one of claims, wherein the AAV capsid has an antigen that is selected from the group consisting of: AAV1, AAV2, AAV3, AAV4, AAV5, AAV6, AAV7, AAV8, AAV9, AAV10, AAV11, AAV12, AAV13, chimeric AAV, genetically engineered AAV, or chemically modified AAV.

In some embodiments, the disclosure provides the method of any one of claims, wherein optionally, the AAV preparation is concentrated and further wherein the preparation is administered at a specific dose to a subject in need thereof.

In another embodiment, the disclosure provides the method of any of the above claims, wherein the heating of step b) is at least at 80° C.

In yet another embodiment, the disclosure provides the method of any of the above claims, wherein the heating of step b) is up to 100° C.

In some embodiments, the disclosure provides the method of any of the above claims, wherein the method of quantifying viral protein and viral DNA is done within about 4 hours.

In another embodiment, the disclosure provides the method of any of the above claims, wherein the viral preparation comprises one or more of full genome-containing virus particles, partial genome-containing virus particles, self-complementary genome-containing virus particle (double stranded genome), and genome-free virus particles.

In one embodiment, the disclosure provides a kit comprising:
a) wash buffer, diluent buffer, elution buffer, DNA ligase enzyme;
b) PCR master mix, PCR assay mix and a set of 3' and 5' primers for quantifying AAV DNA;
c) one or more sets of 3' and 5' probes for detecting and quantifying one or more serotypes of AAV capsid protein, capture beads comprising an antibody that recognizes the AAV capsid, AAV protein standard.

In some embodiments, the disclosure provides the kit described above, wherein the kit measures the concentration of full AAV capsids in an AAV preparation.

In some embodiments, the disclosure provides the kit described above, wherein the AAV capsid has an antigen that is selected from the group consisting of: AAV1, AAV2, AAV3, AAV4, AAV5, AAV6, AAV7, AAV8, AAV9, AAV10, AAV11, AAV12, AAV13, chimeric AAV, genetically engineered AAV, or chemically modified AAV.

In yet another embodiment, the disclosure provides a kit comprising:
a) wash buffer, diluent buffer, elution buffer, DNA ligase enzyme;
b) PCR master mix, PCR Assay mix, two sets of viral DNA primers;
c) one or more sets of 3' and 5' probes for detecting and quantifying one or more serotypes of a virus, capture beads comprising an antibody that recognizes a viral capsid antigen, viral protein standard.

In yet another embodiment, the disclosure provides the kit described above, wherein the kit measures the concentration of full viral capsids in a viral preparation.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the invention are utilized. The following figures and their descriptions constitute a part of the specification and illustrate the exemplary embodiments that are not to be considered limiting to the scope of the invention.

Slope=−3.487, Y-intercept=39.292, $R^2$=0.998 (closer to 1 means most points are on or close to the regressed curve), Efficiency %=93.559. $C_t$ refers to the cycling number for qPCR and indicates the number of cycles for dye detection. The data is based on an average of 3 replicates. Together with the DNA standard curve of 4b, the curves are useful to determine full versus empty viral ratio percentages using Equation 1 (see Example 1).

Figure 4A:
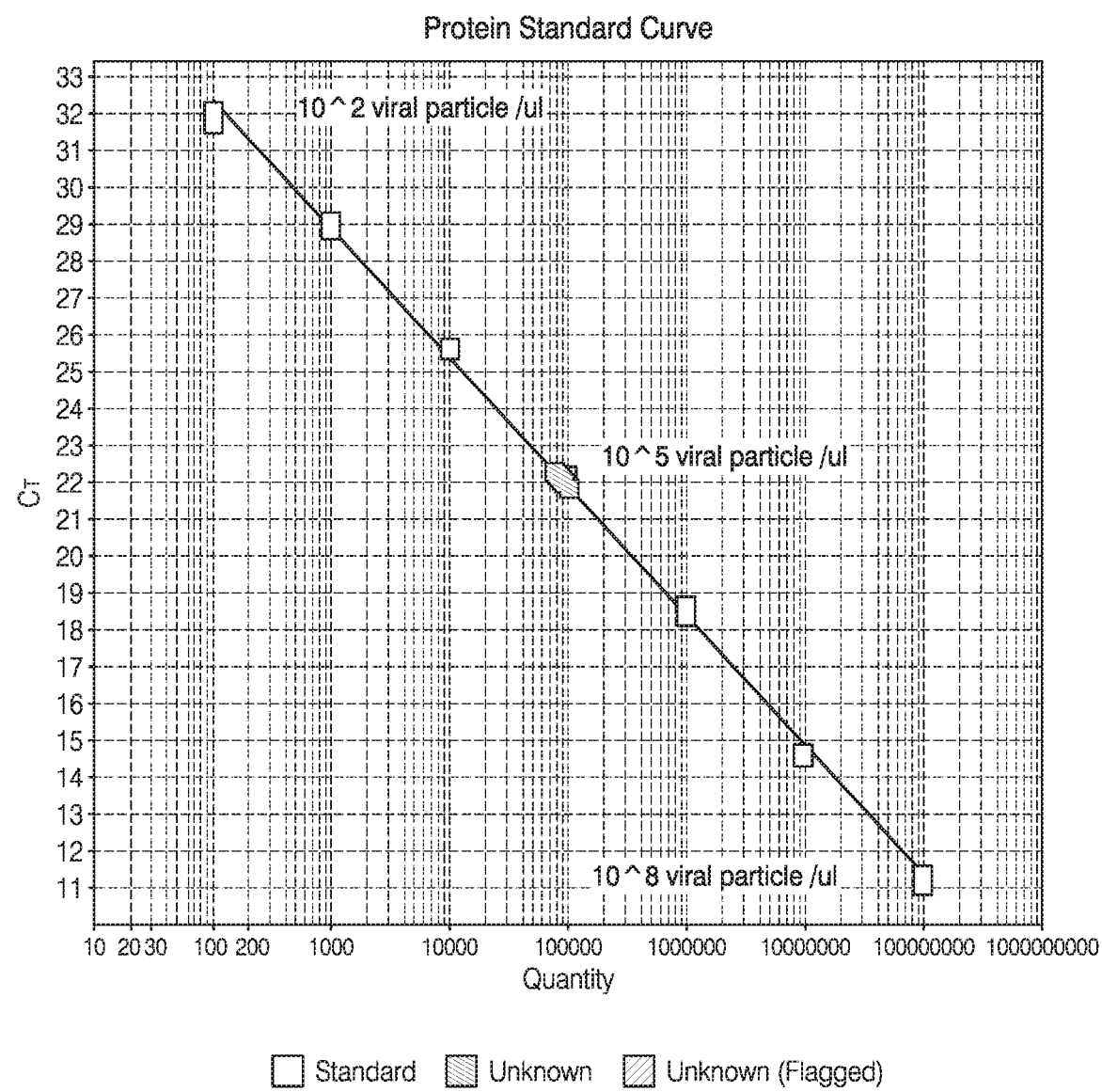
FIG. 4a: Graph showing protein standard curve. An AAV8 viral preparation was used to generate the protein standard curve. Protein amounts were linear in 10 to $10^7$ viral particle/μl concentration range. qPCR instrument set to measure FAM dye fluorescence.
Figure 4B:
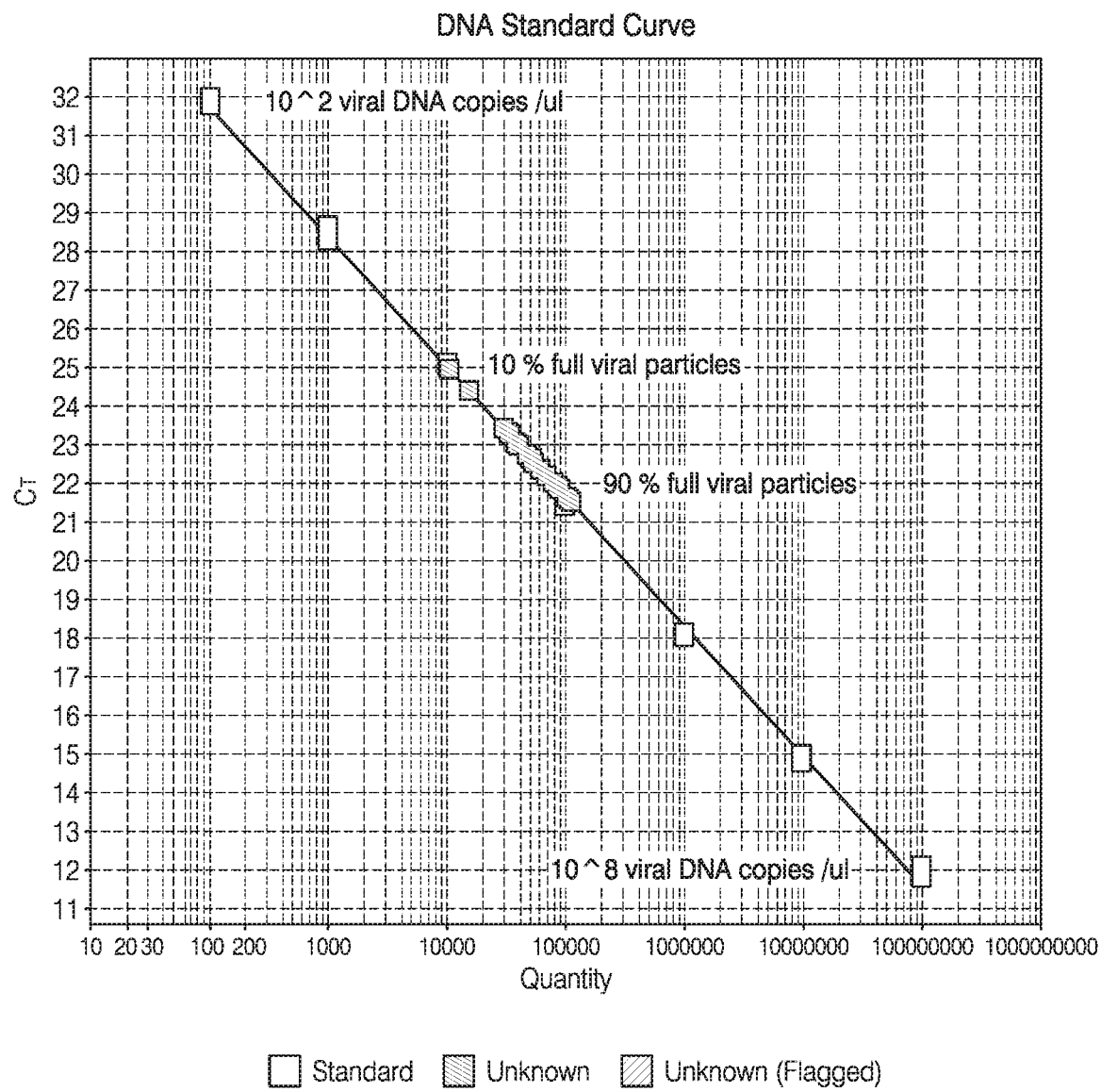

FIG. 4b: Graph showing DNA standard curve. An AAV8 vector preparation is used generate a standard DNA curve. DNA was linear 10-$10^7$ vector copy/μl concentration range. qPCR instrument set to measure VIC dye fluorescence. Slope=−3.344, Y-intercept=38.403, $R^2$=0.999, Efficiency %=99.103. $C_t$ refers to the cycling number for qPCR and indicates the number of cycles for dye detection. The data is based on an average of 3 replicates. In one embodiment, CMV specific sequences are used for AAV expression. Together with the protein standard curve of 4a, the curves are useful to determine full versus empty viral ratio percentages using Equation 1 (see Example 1).

Figure 5:
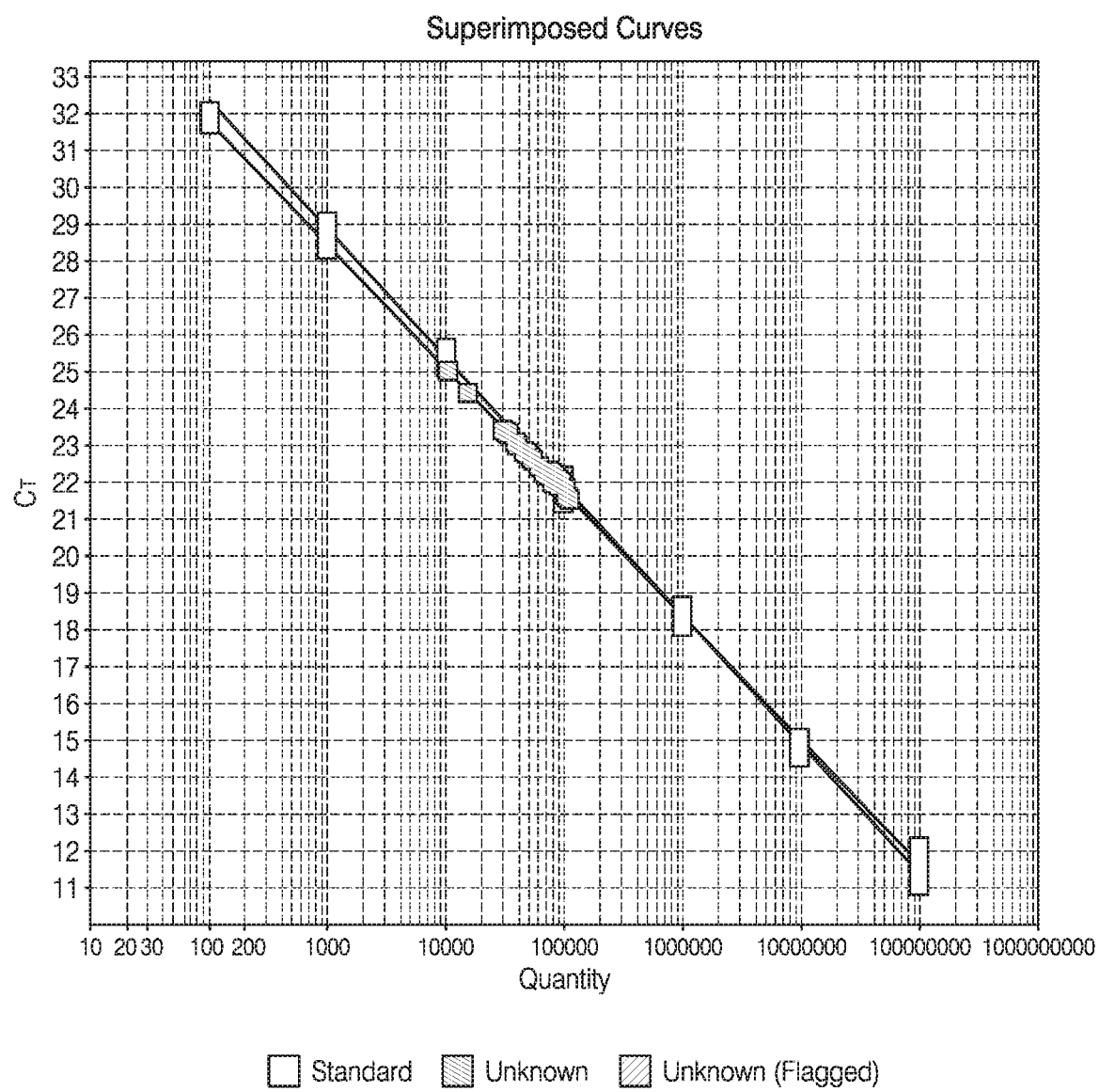

FIG. 5: Detection of AAV8 vector full/empty ratios determined using superimposed protein and DNA standard curves in one reaction. % Full/empty viral vectors can be predicted using Equation 1 of viral DNA quantitation/capsid protein quantitation multiplied by 100. Measuring the capsid protein and DNA together leads to the simple, fast, and direct determination of a virus, for e.g., AAV virus full and empty ratio with a time-to-result of about 4 hours.

DETAILED DESCRIPTION OF THE INVENTION

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations and embodiments pertaining to the elements of the compositions or methods described herein are specifically enumerated by the present disclosure and are disclosed herein just as if each and every combination was individually and explicitly disclosed; to the extent that such combinations are not in conflict with one another. In addition, all subcombinations of the elements of the compositions or methods described herein are also specifically enumerated by the present disclosure and are disclosed herein just as if each and every sub-combination was individually and explicitly disclosed herein; to the extent that such sub-combinations are not in conflict with one another.

DEFINITIONS

In describing certain embodiments of the present disclosure:

A feature of AAV vector generation in cell culture is the formation of an excess of "empty" capsids, which lack the vector genome. In certain embodiments, the amount of empty capsids is assessed in order to accurately determine the concentration, dose, and/or potency of an AAV preparation. Empty capsids can also be considered as product related impurities, which should be reduced during purification. In certain embodiments, it is important to determine the total amount of empty capsids to reduce an innate and/or adaptive immune response against the capsid antigen.

In some embodiments, the methods described herein can be applied to any viral assay and is not limited to AAV only; for e.g., for the determination of viral vector product quantity (particles/mL) and quality (% full/empty) of viruses including but not limited to: such as parvovirus, adeno-associated virus (AAV), adenovirus, HIV, MMV, lentivirus, retrovirus, herpesvirus, poxvirus, paramyxovirus, baculovirus, reovirus, alphavirus, flavivirus, and combinations thereof.

In some embodiments, the assay may detect one, several or all the viral serotypes of a virus depending on the detection antibody's recognition capacity of the various serotypes. The 'detection antibody' may be engineered to recognize one or more serotypes. In a particular embodiment where AAV full:empty ratios are measured, the assay utilizes the AAVX antibody which is a camelid antibody that is found to bind multiple serotypes of AAV, namely one or more of the 13 known AAV serotypes (hence, it is sometimes also called the universal AAV antibody). In certain assays, additional anti-AAV antibodies can be included in the assay to detect additional AAV serotypes. In some embodiments, only one AAV antibody (like AAVX) directed to several of the 13 AAV serotypes may be used in the assay.

In order to detect viral capsid protein, in some embodiments, each detection antibody is coupled to an oligonucleotide sequence (3' oligo and 5' oligo respectively). In a preferred embodiment, at least two detection antibodies are employed, the antibodies detecting at least one serotype. In other embodiments, multiple sets of 3'-5'-tagged detection antibodies may be used, each set recognizing a different serotype. In a most preferred embodiment, the at least two detection antibodies are capable of detecting multiple serotypes, for e.g., the AAVX antibody that is known to recognize serotypes AAV1 to AAV 13. The 3' oligo and 5' oligo are brought into close proximity by a "splint probe". (In FIG. 3b, see the black arc above hatched semicircle. The hatched semicircle depicts the 3' and the 5' oligonucleotides (attached to the antibody). The attachment is via biotin coupling. The splint probe guides the 3' and the 5' oligonucleotides next to each other so that the DNA ligase enzyme can ligate the nick and join the oligonucleotides. Now, the PLA (Proximity Ligation Assay) can be performed using primers (shown as dumbbell shape: the open circle is say the 3' primer and the hatched circle is the 5' primer) specific to the ligated DNA which indirectly correspond as "protein probes". In order to detect viral capsid protein, in some embodiments, primers specific for the ligated oligo is amplified and detected by FAM fluorescence and quantified.

Correspondingly, in some embodiments, to detect the released viral DNA, primers specific for the viral DNA is amplified and detected by VIC fluorescence and quantified.

In some embodiments, the MasterMix used in qPCR comprises the dye-labelled primers, the polymerase amongst other components necessary for the TaqMan assay. The DNA ligase is added separately.

In some embodiments, the capture and/or the detection antibodies are derived from any species, including but not limited to rat, mouse, rabbit, hamster, monkey, chimpanzee, horse, cow, cat, chicken, human, humanized, pig, camelid, chimeric, etc.

In some embodiments, the capture antibody which recognizes one or more serotypes of a virus, can be attached to a capture surface via chemical (including but not limited to, sulfhydyl reactive-, carbonyl reactive-, amine reactive-, etc.) means, via affinity means or via physical means. In a preferred embodiment, the capture antibody is biotinylated which in turn attaches to a streptavidin-activated surface. As the skilled artisan would know, alternately, any affinity conjugation ligands can be utilized to achieve a similar result of binding capture antibody to surface.

In some embodiments, capture is limited to magnetic beads alone. In other embodiments, capture can be on any solid surface used to capture viral proteins and/or capsids, including but not limited to: plates, tube, film, membrane, well, glass surface, bead, resin, microfluidic sheet, etc.

DETAILED DESCRIPTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Recombinant viral vector preparations can contain different levels of full or partial genome-containing particles as well as empty virions. Such particle diversity can be attributed to multiple factors such as genome packaging efficiency, production methods, downstream purification techniques and storage conditions. In therapies employing viral vectors for e.g., gene therapy, there exists a potential for vector dose-related immunotoxicity in patients. In viral production, empty virions are inadvertent by-products of recombinant packaging process, resulting in vector lots with mixtures of full and empty virions at variable ratios. Present methods for accurately determining the quantity (particles/mL) of vectors have their limitations. For e.g., current ELISA methods show poor accuracy and precision and can only measure a fraction of the viral serotypes. A combination of ELISA and qPCR is available, but it provides a convoluted approach with high margins of error. Analytical Ultracentrifugation (AUC) methods like CsCl gradients are not desirable for the following reasons: they are extremely slow, tedious, low throughput, capital intensive, require large samples of high purity and substantial user training and expertise. Electron Microscopy (TEM) similarly involves tedious sample prep, skilled expertise and is very slow and expensive. Besides, neither AUC or TEM are amenable to high-throughput analysis.

Adeno-Associated Virus (AAV) is a commonly used vector of choice in gene therapies. It is a preferred vector because it is non-pathogenic, non-toxic, can infect non-dividing and dividing cells, the virus persists, several serotypes are available, has a simple vector design for cost effective manufacturing is highly precise and specific for target cell delivery. Current AAV ELISA assays can only detect 6 of 13 AAV serotypes. Therefore, there is a need for a single, streamlined assay that is accurate and reliable for the determination of viral vector quantity (particles/mL) and quality (% full/empty) for a large number of viral serotypes.

In some embodiments a qPCR-based dual or duplex assay that quantitates DNA, e.g. viral DNA and protein (viral capsid protein) in a single assay is described. In other words, the assay simultaneously determines vector quantity (particle titer) and quality (full & empty) rapidly and in a streamlined workflow producing excellent data quality with accuracy and precision. The assay can measure most of the 13 AAV serotypes and the assay can measure crude samples directly with no sample prep. The assay may be performed manually as demonstrated in Example 1. Alternatively, the assay may use hardware/software for e.g., an automated, magnetic bead processing unit (such as the KingFisher™ Flex instrument), a qPCR instrument (e.g., 7500 Fast PCR instrument), to achieve an automated or semi-automated hands-off workflow. In one embodiment, the disclosure is directed to a kit comprising the necessary reagents and buffers for the duplex assay for determining full/empty viral vector and/or to quantitate a viral particle titer.

EXAMPLES

In some embodiments, the disclosure describes an efficient and accurate analytical method for AAV vector titer, especially empty/full ratio determination, is still lacking. Existing analytical solutions that offer indirect empty/full determination are extremely slow, tedious, are capital intensive, require large samples of high purity, and high levels of user training and expertise. Here we describe a dual/duplex assay that is designed to enable the simultaneous quantitation of vector DNA by TaqMan assay and viral capsid (protein) determination by proximity ligation assay (PLA). This leads to the simple, fast, and direct determination of AAV full and empty ratio with a time-to-result of about 4 hours. Both protein and DNA can be quantitated at the same time. This novel approach represents a paradigm shift in AAV analytics, and enables the end-user to accelerate their work by obtaining vital information about vector samples with unprecedented speed, ease, and accuracy.

In other embodiments, the methods described herein can be applied to any viral assay and is not limited to AAV only; for e.g., for the determination of viral vector product quantity (particles/mL) and quality (% full/empty) of any virus such as parvovirus, adeno-associated virus (AAV), adenovirus, lentivirus, retrovirus, herpesvirus, poxvirus, paramyxovirus, baculovirus, reovirus, alphavirus, flavivirus, and combinations thereof. Moreover, the assay may detect one, several or all the viral serotypes of a virus depending on the detection antibody's recognition capacity of the various serotypes. The detection antibody may be engineered to recognize one or more serotypes.

Figure 1:
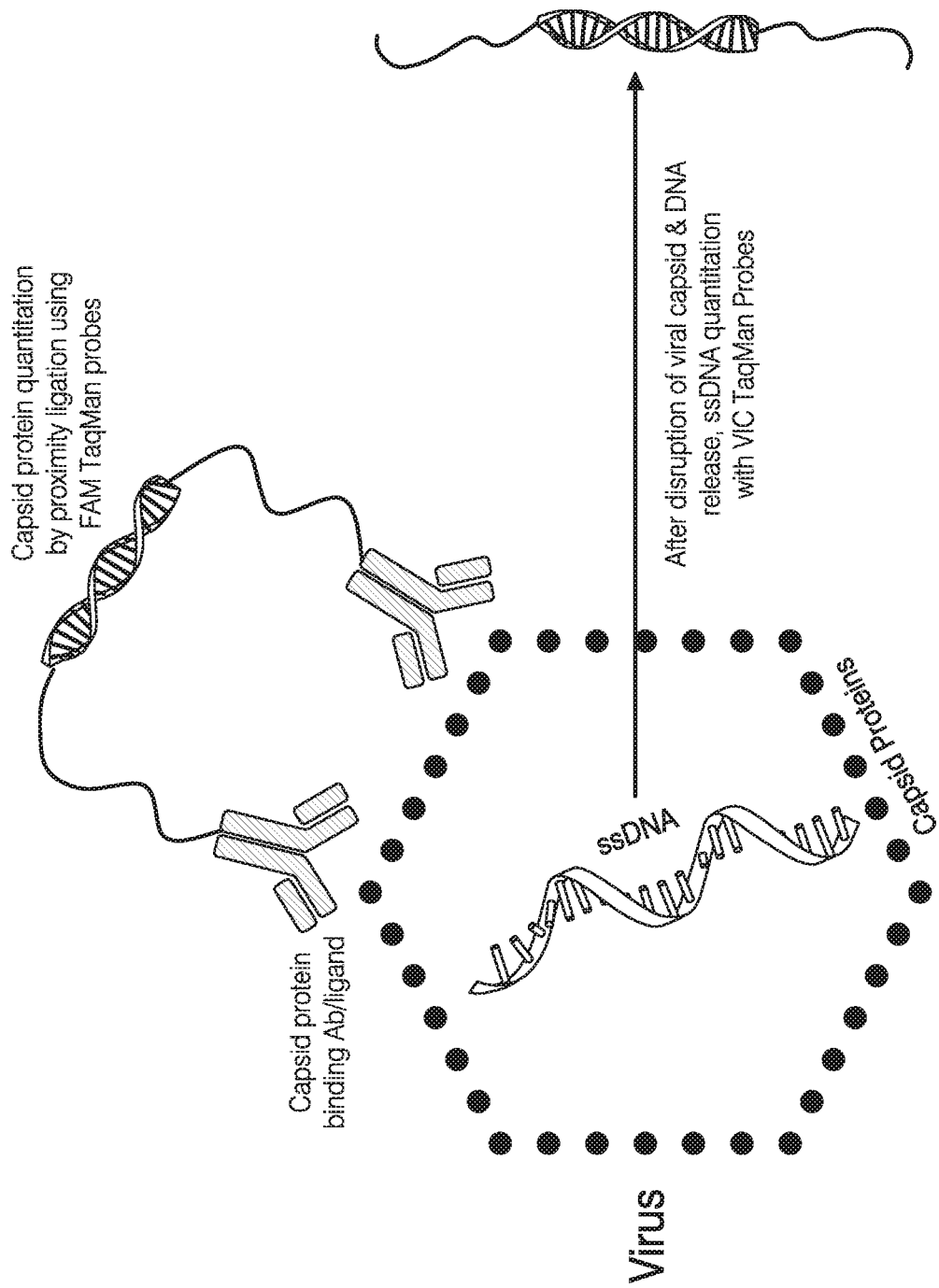
FIG. 1: This shows the principle of the virus dual/duplex assay. Viral capsid protein is quantified by a PLA (Proximity Ligation Assay) using two specific detection antibodies to the viral capsid protein. Each detection antibody is also coupled to an oligonucleotide sequence (oligo 1 and oligo 2). The oligonucleotide sequences are brought together using a 'splint probe'. The nick is ligated using DNA ligase. The ligated sequence is amplified and quantified by quantitative PCR (qPCR) to give a protein readout. After protein quantification, the viral capsid assembly is disrupted to release the viral DNA, which is quantified by another qPCR assay using nucleic acid primers tagged with another dye e.g., VIC dye. Thus, both protein and DNA can be quantified in the same container one after the other.

The principle of this assay is described in FIG. 1. In this assay, protein amounts, e.g. viral capsid protein are quantified using a PLA (Proximity Ligation Assay) using two detection antibodies specific to the viral capsid protein, wherein each detection antibody is also coupled to an oligonucleotide sequence (a 3' oligo that is biotin conjugated to the detection antibody, and a 5' oligo also biotin conjugated to the detection antibody). The two dye-tagged oligonucleotide sequences are brought together using a 'splint probe', and the nick is ligated using DNA ligase. Oligonucleotide primers specific for the ligated oligo 3'+oligo 5' sequences (indirectly identifying the viral capsid protein) and which are tagged with a first dye, for e.g., FAM dye, is amplified and quantified by quantitative PCR (qPCR) to give a viral capsid protein readout. qPCR fluorescence readouts are much more robust, sensitive and much faster than ELISA readouts.

Subsequently after protein related amplification, the viral capsid assembly is disrupted to release the viral DNA. In one embodiment, the capsid disruption is achieved through heat denaturation (anywhere between 80 to 100° C., depending on the virus); alternatively, the capsid disruption can be done using enzyme digestion e.g., proteinase. The capsid disassembly releases the viral DNA which is quantified by a second qPCR assay, this time using oligonucleotide primers specific for the viral DNA and which are tagged with another dye e.g., VIC dye. Thus, in this assay, both protein and DNA can be quantified in the same container one after the other.

Figure 2:
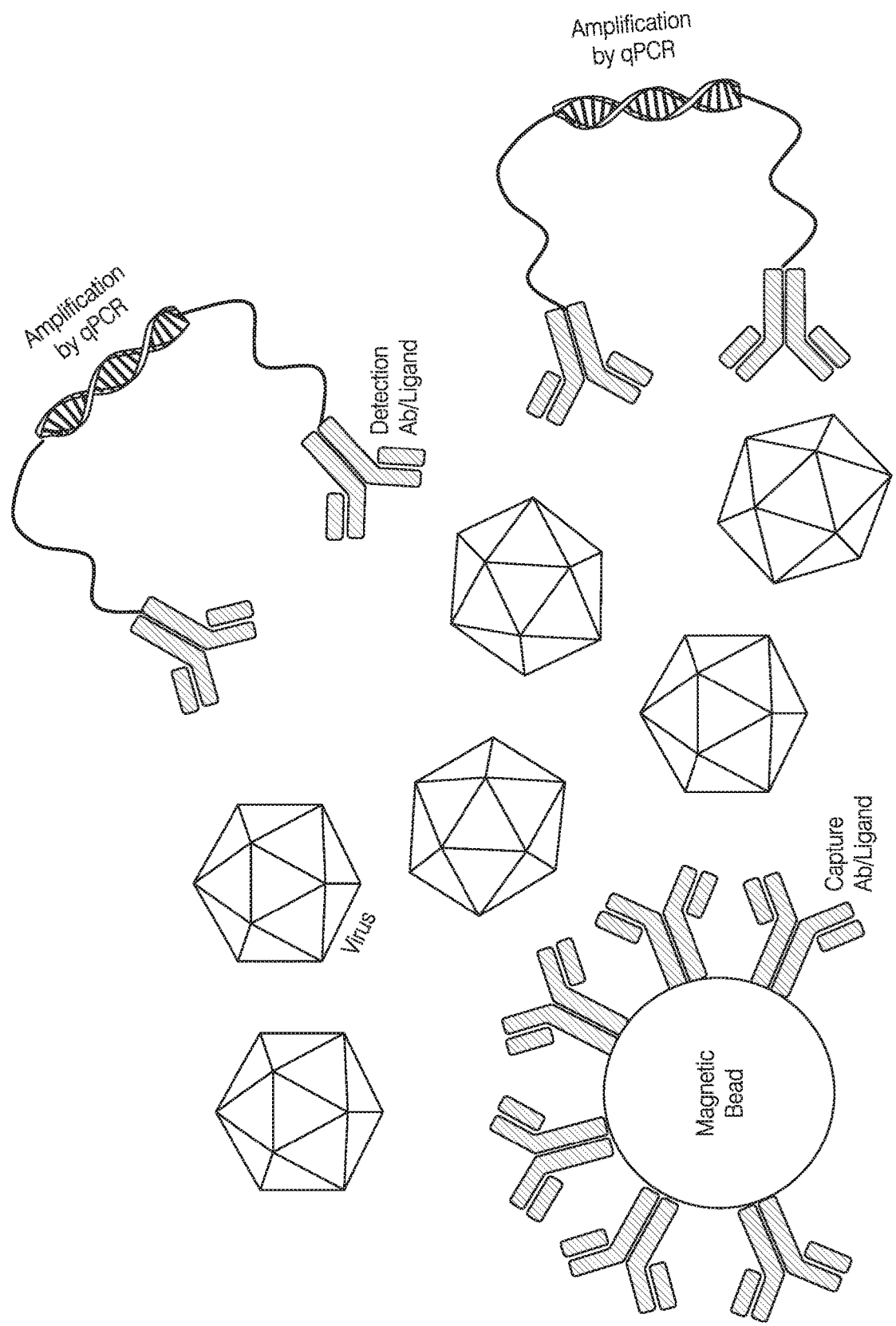
FIG. 2: This figure shows overall how viral capsid proteins are captured in a separation/purification workflow. Magnetic beads with capture antibody capture the viral capsids. The viral capsid protein amounts are quantified by PLA (Proximity Ligation Assay) as described above.

FIG. 2 shows further details of how viral capsid proteins are captured in the first step for PLA. In this experiment, Dynabeads® MyOne™ Streptavidin T1 magnetic beads, with AAVX capture antibody was used. The viral capsid protein is recognized by the AAVX antibody and captured. Then wash step are performed to removed non-specific binding. Then two additional detection antibodies are used which bind the capsid. Each detection antibody is also coupled to an oligonucleotide sequence (3' oligo and 5' oligo respectively). The 3' oligo and 5' oligo are brought into close proximity by a "splint probe" (In FIG. 3b, see the black arc above hatched semicircle. The hatched semicircle depicts the 3' and the 5' oligonucleotides that are biotin coupled to the detection antibody). The splint probe guides the 3' and the 5' oligonucleotides together next to each other so that the DNA ligase enzyme can ligate the nick and join the oligonucleotides. Now, the PLA (Proximity Ligation Assay) can be performed using primers (shown as dumbbell shape: the open circle is say the 3' primer and the hatched circle is the 5' primer) specific to the ligated DNA which indirectly correspond as "protein probes". Using the primers, the ligated DNA is amplified, detected by FAM fluorescence and thus, the viral capsid proteins are quantified. Capture is not limited to magnetic beads only: any solid surface can be used to capture viral proteins and/or capsids, including but not limited to: plates, tube, film, membrane, well, glass surface, bead, resin, microfluidic sheet, etc.

Figure 3A:
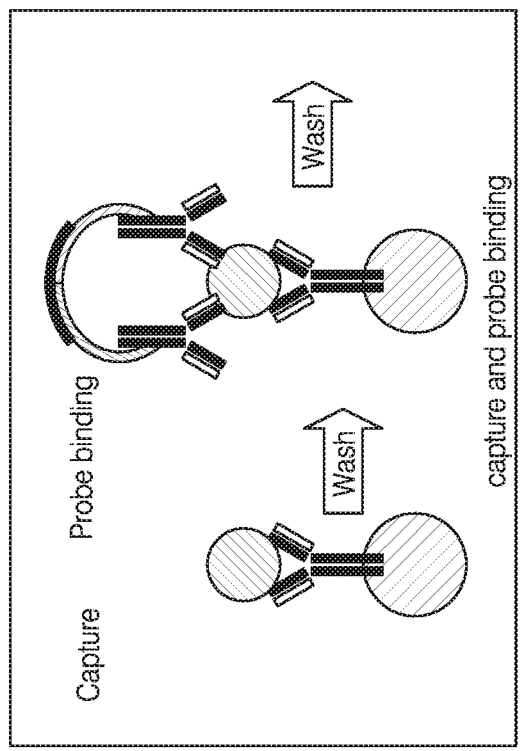
FIG. 3a: This figure is a detailed diagrammatic representation of how a viral capsid protein (smaller cross hatch circle) is captured by a capture antibody on a magnetic bead (larger cross hatch circle). After washes, two detection antibodies coupled with oligonucleotide sequences are shown. The dark black filled arc represents the 'splint probe' that aids to bring the oligonucleotide sequences close together.
Figure 3B:
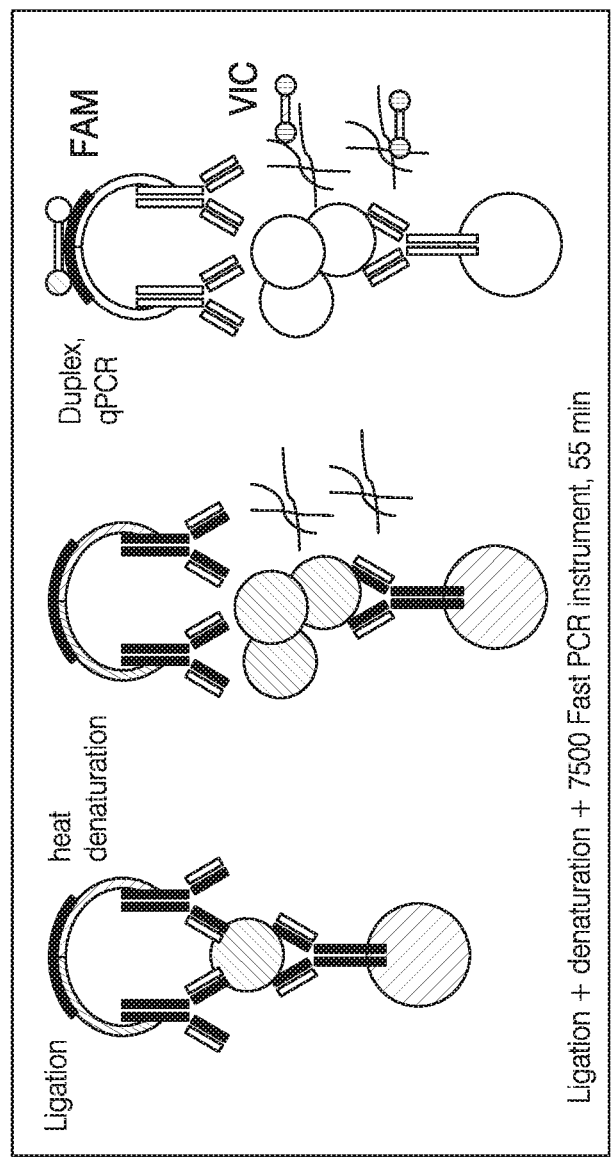
FIG. 3b: The diagram on the left continues from 3a above, where the oligonucleotide sequences are ligated with DNA ligase, quantified by PLA (Proximity Ligation Assay) as described above and is shown in the middle panel. Due to heat denaturation, the viral DNA is released (irregular lines). Moving on to the last panel, the magnetic beads, viral capsid etc. fall apart due to heat denaturation (shown as open circles). Another set of 3' and 5' primers to the viral DNA is added. These primers are tagged with another dye e.g., VIC dye, and is quantified by another qPCR assay to give a viral DNA readout in the same container or in a single assay.

FIG. 3b also shows how the viral capsid assembly is disrupted to release the viral DNA after protein related amplification has been performed. In one embodiment, the capsid disruption is achieved through heat denaturation (between about 80 to about 100° C., depending on the viral capsid disassembly properties). Alternatively, capsid disruption is done using enzyme digestion e.g., proteinase. Capsid disassembly releases the viral DNA within, which is quantified by a second qPCR assay, this time using 3' and 5' oligonucleotide primers specific for the viral DNA (see dumbbell next to the wavy lines which depicts viral DNA). The 3' and 5' oligonucleotide primers (shown as hatched small circles) are specific for the viral DNA and comprise another dye e.g., VIC dye, so viral DNA quantification is done on a different fluorescent channel. Thus, in this assay, both protein and DNA can be quantified in the same container one after the other.

Example 1: Exemplary Single Streamlined Manual Assay for Measuring AAV Viral Vector Described herein is an assay that enables the accurate and reliable determination of AAV vector product quantity (particles/mL) and quality (% full/empty) for several AAV serotypes. An AAVX antibody was used in this assay, which can recognize serotypes AAV1 through AAV9 and numerous recombinant and chimeric serotypes (from ThermoFisher Scientific, cat. number 810352201 or 810352210). A second AAV antibody referred to as AAVY herein, was also used in the assay (from any of ThermoFisher Scientific, cat. numbers 810338001, 810338010, 810333001 and 810333010). It is to be understood that the antibody reagents used herein is for the purpose of describing particular embodiments only, and is not intended to be limiting. As the skilled artisan would recognize, the protocol can be performed using any AAV antibody derived from any species, including but not limited to rat, mouse, rabbit, human, camelid, chimeric, etc. In addition, one would also recognize that one or multiple AAV antibodies directed to one or more 13 AAV serotypes can also be used.

AAV8 vectors were obtained from Virovek, Inc. and University of North Carolina were used as AAV virus DNA standards to confirm DNA copy number, and to evaluate and confirm assay accuracy.

TABLE 1

Shown below are a set of exemplary reagents used in this manual assay.

| Table 1: Reagents | Quantity | Storage |
|---|---|---|
| AAVX 5' PROBE | 1 Tube, 350 μL | −15° C. to −25° C. |
| AAVX 3' PROBE | 1 Tube, 350 μL | −15° C. to −25° C. |
| AAVY 5' PROBE | 1 tube, 350 μL | −15° C. to −25° C. |
| AAVY 3' PROBE | 1 Tube, 350 μL | −15° C. to −25° C. |
| AAVX Ligation and Assay Mix | 1 Tube, 600 μL | −15° C. to −25° C. |
| DNA Ligase | 1 Tube, 55 μL | −15° C. to −25° C. |
| AAVX Standard (1 × 10$^7$ copies/μL) | 1 Tube, 400 μL | Shipping −20° C.; Store at; 2° C. to 8° C. after first use |
| AAVX Elution Buffer | 1 Tube, 7 ml | 2° C. to 8° C. |
| AAVX Capture Beads | 1 Bottle, 5.25 ml | 2° C. to 8° C. |
| AAVX Diluent Buffer | 1 Bottle, 50 ml | 2° C. to 8° C. |
| AAVX Wash Buffer | 1 Bottle, 100 ml | 2° C. to 8° C. |
| TaqMan Fast Master Mix 2X | 1 Bottle, 6 ml | 2° C. to 8° C. |

First, AAVX Standard Dilution is done as follows: Prepare serial dilutions in 2 mL Eppendorf tubes as shown in Table 1 below. Add the respective amounts of AAVX Diluent to each tube. Tube NPC (Non-Protein Control) contains the Diluent only and serves as the Non-Protein Control (NPC). For the rest of the Standard tubes, add the appropriate amount of AAVX particles. Mix dilutions well by vortexing and then briefly spin down the tube contents to the bottom.

TABLE 2

Serial dilution of AAVX Standard with 3 replicates

| Table 2 | AAVX Particles | AAVX (μL) | AAVX Diluent to be Added (μL) | Total (μL) |
|---|---|---|---|---|
| Std 1 | 1.00E+07 | 120 | 0 | 120 |
| Std 2 | 1.00E+06 | 12 μL of Std 1 | 108 | 120 |
| Std 3 | 1.00E+05 | 12 μL of Std 2 | 108 | 120 |
| Std 4 | 1.00E+04 | 12 μL of Std 3 | 108 | 120 |
| Std 5 | 1.00E+03 | 12 μL of Std 4 | 108 | 120 |
| Std 6 | 1.00E+02 | 12 μL of Std 5 | 108 | 120 |
| Std 7 | 1.00E+01 | 12 μL of Std 6 | 108 | 120 |
| NPC | | | 120 | 120 |

The present protocol is performed on a sample plate. However, as would be recognized by one of skill in the art, the protocol can be applied to any type of container, for e.g., plates, slides, tubes, wells, microfluidic devices, arrays, dishes, films, depressions on any flat surface, etc.

Preparation of Sample Plate

Dispense 20 μL AAVX Capture Beads into each Standard and Sample wells. Next, dispense 30 μL of each Standard, starting with NPC, into each of the respective Standard wells. Make several dilutions of your Unknown samples using the AAVX Diluent Buffer and dispense 30 μL of those samples into the Unknown wells in triplicate. Mix really well. Let the plate sit on the bench for 1 hour. Every 15 minutes, pipette up and down and mix well again to re-suspend beads and samples.

Next, prepare Sample Plate (PCR-compatible plate). Resuspend AAVX Capture Beads by pipetting or place tube on a rotator for about 10-15 minutes until all the beads are resuspended. Transfer AAVX Capture Beads into a reservoir and dispense 20 μL into each Standard and Sample wells using a 200 μL multi-channel pipette (manual or electronic). Dispense 30 μL of each Standard, starting with NPC, into each of the respective Standard wells. If necessary, dilute unknown samples using the AAVX Diluent Buffer and dispense 30 μL into the Unknown wells in triplicate. Using a manual pipette with volume set to 40 μl, pipette each well up and down 10 times to mix, minimize bubbles during mixing. Incubate the sample plate for 1 hour at room temperature. Pipette mix (10 times) every 30 minutes using a manual 200 μL multi-channel pipette (set the volume at 40 μl) for a total of 3 times (at time 0, 30 and 60 minute during the incubation period).

2× Wash Steps

After capture step, briefly spin the plate in a plate centrifuge, place sample plate on a magnetic plate until all beads are magnetized (~1 minute, the beads are on the well of the plate not at the bottom). While the plate is on the magnetic stand, remove the liquid from the center of the well using a manual pipet with volume set to 60 μl. Add 100 μL of Wash Buffer to plate. Resuspend beads by pipetting up and down 10 times on all four corners of each well. Once beads are fully resuspended, place sample plate on the magnetic stand until solution is clear (~1 minute) and removes the Wash Buffer while the plate is on the magnetic stand (set the volume to 110 μl). Repeat this process once more. After the second wash step, remove the entire wash buffer then take the sample plate off the magnetic stand.

Probe Solution for Detection

Prepare probe mix in 5-ml tubes as shown in Table 3. Adjust based on sample numbers. Mix the Probe solution by inverting the tube 8 times. Transfer Probe solution into a reservoir and dispense 50 μL to each well of the sample plate using a 200 μL multi-channel pipette (manual or electronic). Resuspend beads by pipetting up and down 10 times on all four corners of each well (be sure the pipette tips touch all corners of the wall to ensure complete resuspension of beads, using a multi-channel manual pipet and set the volume at 40 μl). Incubate sample plate at room temperature for 30 mins with mixing 10 times every 15 minutes (total 3 times, at time 0, 15 and 30 minutes).

TABLE 3

Probe Solution

| Reagent | Volume/ reaction | 48 reactions | 96 reactions |
|---|---|---|---|
| ProteinSEQ Diluent Buffer | 56.2 μL | 2700 μL | 5400 μL |
| AAVX 5' PROBE | 1.6 μL | 75 μL | 150 μL |
| AAVX 3' PROBE | 1.6 μL | 75 μL | 150 μL |

TABLE 3-continued

Probe Solution

| Reagent | Volume/reaction | 48 reactions | 96 reactions |
|---|---|---|---|
| AAVY 5' PROBE | 1.6 μL | 75 μL | 150 μL |
| AAVY 3' PROBE | 1.6 μL | 75 μL | 150 μL |
| Total | 62.5 μL | 3000 μL | 6000 μL |

Repeat 2× Washes (Same as Before).

After Probe detection step, briefly spin the plate in a plate centrifuge (when the spin speed reaches 800 rpm, stop the spin). Place sample plate on a magnetic plate until all beads are magnetized (~1 minute, the beads are on the well of the plate not at the bottom). While the plate is on the magnetic stand, remove the liquid from the center of the well using a manual pipette with volume set to 60 μl). Remove sample plate from the magnet stand and add 100 μL of Wash Buffer. Resuspend beads by pipetting up and down 10 times on all four corners of each well (set up pipette volume at 90 μL, see FIG. 1; be sure the pipette tips touch all corners of the wall to ensure complete resuspension of beads). Once beads are fully resuspended, place sample plate on the magnetic stand until solution is clear (~1 minute) and removes the Wash Buffer while the plate is on the magnetic stand (set the volume to 110 μl). Repeat this process once more. After the second wash step, remove the entire wash buffer then take the sample plate off the magnetic stand.

Elution, Ligation and PCR Preparation

Transfer Elution Buffer to a plate reservoir, and dispense 15 μL to each well of the plate using a 20 μL or 200 μL multi-channel pipette (manual or electronic). Prepare qPCR mastermix as shown in Table 4. Adjust according to sample number with 20% for overage. Transfer mastermix into a reservoir and dispense 15 μL into each well. Resuspend beads by pipetting up and down 10 times on all 4 corners of each well (be sure the pipette tips touch all corners of the wall to ensure complete resuspension of beads, using a multi-channel manual pipette and set the volume to 25 μl). Seal the plate, and then spin down the plate in a plate centrifuge for 3 seconds at 500 rpm (hold Short button and let go when it reaches 500 rpm). Proceed to the Real-time PCR Instrument.

TABLE 4A

Prepare Mastermix.

| Components | Volume/reaction | 48 Reactions | 96 Reactions |
|---|---|---|---|
| 2x FAST master mix | 20 μL | 960 μL | 1920 μL |
| AAVX Ligation and Assay mix | 2 μL | 96 μL | 192 μL |
| ProteinSEQ Ligase | 0.2 μL | 9.6 μL | 19.2 μL |
|  | 22.2 μL | 1065.6 μL | 2131.2 μL |

Table 4B below is an alternative when using their other primer and probe for the DNA target (ITR, other GOI, etc.) instead of using the CMV-targeting primer/probe set used in Table 4A above.

TABLE 4B

Prepare Mastermix

| Components | Volume/reaction | 48 Reactions | 96 Reactions |
|---|---|---|---|
| 2x FAST master mix | 20 μL | 960 μL | 1920 μL |
| AAVX Ligation and Assay mix | 2 μL | 96 μL | 192 μL |
| other primer and probe mix* | 2 μL | 96 μL | 192 μL |
| ProteinSEQ Ligase | 0.2 μL | 9.6 μL | 19.2 μL |
|  | 22.2 μL | 1065.6 μL | 2131.2 μL |

* The probe used should be VIC-labeled, and the primer and probe concentrations are 20× so the final concentrations of primer and probe in qPCR reaction are 1×. Load the Sample plate onto the Real-Time PCR instrument. If using AccuSEQ software, proceed with the steps below. If using other Real-time Instruments, follow the Instrument's User Guide. Perform PCR using AccuSEQ Software, the AAV8-Alpha-test-template, AccuSEQ 2.1 software on the computer connected to a 7500 Fast PCR instrument. Use the Define and Set up Standards to set up the standard curve. Click on Define and Set Up Standards, enter Standard Curve Information (7 points, 3 replicates, 1e7 starting quantity and 1:5 dilution). Set thermal cycling conditions as: Hold 37° C. 10 minutes; Hold 95° C. 3 minutes; 40 cycles; 95° C. 3 seconds; 60° C. 30 seconds. Press run.

The run file generates two standard curves: DNA curve (FIG. 4b) and Protein curve (FIG. 4a). The DNA curve flows linear regression and protein curve flows 4PL regression.

On standard curve page, select all reactions in the standard curve, select linear for curve fit (which is for DNA measurement). Click Analysis. Save the file and export the data and name the file as "DNA data".

On standard curve page, select all reactions in the standard curve, select the 4PL regression for protein analysis. Click Analysis. Save the file and export the data and name the file as "Protein data". To analyze the data, add a new excel sheet to the protein data file, name the new sheet as "analyzed sheet" and copy the following columns from the protein data file first sheet to the new sheet (analyzed sheet), sample name column, target column, quantity column. Then sort the three column data first by target, then by sample name (from A to Z option). Open DNA data file. Add a new excel sheet to the DNA data file, name the new sheet as "analyzed sheet" and copy the following columns from the DNA data file first sheet to the new sheet (analyzed sheet), sample name column, target column, quantity column. Then sort the three column data first by target, then by sample name (from A to Z option).

Open the AAV8 analysis calculation spreadsheet associated with this protocol (provided in your Alpha Test Package). In the paste sheet, copy all the sample names from protein data file, analysis sheet under the sample name of analysis calculation spreadsheet. Then copy all the DNA quantity data from DNA data file analysis sheet under DNA quantity in the analysis calculation spreadsheet. Then copy all the Protein quantity data from Protein data file analysis sheet under Protein quantity in the analysis calculation spreadsheet. The analysis calculation spreadsheet will calculate all the parameters in the quantity sheet.

Two standard curves: i) Protein (FIG. 4a) and ii) DNA (FIG. 4b) are generated using different dilutions of viral particle (capsid protein determination) and viral vector (for viral DNA) and the standard curves are plotted. To predict whether viral vector is full or empty, or to calculate the % fullness, Equation 1 is used.

$$\frac{\text{Viral DNA quantitation readout}}{\text{Viral protein quantitation readout}} \times 100 = \% \text{ full capsid} \quad \text{Equation 1}$$

Spike experiments of known quantities of full/empty vectors were used to standardize and evaluate the accuracy and sensitivity of the assay. The accuracy of one such experiment is shown below in Table 5, column 2. The Standard Deviation is shown in column 2 and column 3 is a measure of replicate precision CV %=S.D./Average*100. This shows that the protein-DNA dual assay is both accurate and sensitive at least over 10 to $10^7$ viral particle/μl protein concentration range, and over 10-$10^7$ vector copy/μl DNA concentration range.

TABLE 5

| input sample | assay readout average (%) | assay readout S.D. | assay readout CV % |
|---|---|---|---|
| 10% full viral particle | 10.19% | 0.0051 | 5.00 |
| 20% full viral particle | 21.06% | 0.0173 | 8.23 |
| 30% full viral particle | 34.40% | 0.0189 | 5.51 |
| 40% full viral particle | 44.49% | 0.0145 | 3.25 |
| 50% full viral particle | 54.76% | 0.0310 | 5.67 |
| 60% full viral particle | 59.95% | 0.0526 | 8.77 |
| 70% full viral particle | 68.66% | 0.0111 | 1.62 |
| 80% full viral particle | 83.05% | 0.0757 | 9.12 |
| 90% full viral particle | 95.42% | 0.0581 | 6.09 |
| 100% full viral particle | 106.42% | 0.0132 | 1.24 |

Deducing from the standard curves of FIGS. 4a and 4b, Equation 1 is used to calculate % fullness of a virus. For example, if for a given unknown, the protein readout is $10^7$ protein and the corresponding DNA readout is also $10^7$ DNA, using the equation, we get a ratio of 1, which means that the viral capsid is 100% full. In another example, if for a given unknown, the protein readout is $10^5$ protein and the corresponding DNA readout is $10^3$ DNA, from Equation 1, we get a ratio of 1:100=0.01, which means that the viral capsid is 1% full. And in yet another example, if for a given unknown, the protein readout is $10^6$ protein and the corresponding DNA readout is $10^7$ DNA, from Equation 1 we get a ratio of 10, which means that the viral capsid is 110% full, and so on.

Besides gene therapy applications, the assay is applicable to a variety of procedures routinely used to detect DNA and protein during vaccine production, including but not limited to: i) viral dose determination; ii) lot-to-lot testing; iii) shelf-life testing; iv) viral serotype identification, etc. It is also useful for the capture/detection/quantitation of any proteinaceous target for e.g. aptamers. This assay is particularly useful for detection and quantitation in vaccine production.

The examples were intended to illustrate, but not limit certain embodiments of the disclosure. One skilled in the art will understand that various modifications are readily available and can be performed without substantial change in the way the invention works. All such modifications are specifically intended to be within the scope of the invention claimed herein.

What is claimed is:

1. A method of quantifying a dose of a viral preparation, comprising:
    a) quantifying a total number of viral capsids in the viral preparation via a viral-specific proximity ligation assay (PLA) assay;
    b) heating the viral preparation to enable disassembly of the viral capsid, and releasing the viral DNA; and
    c) quantifying the total amount of viral DNA in the viral preparation via a viral DNA-specific quantitative PCR assay, wherein the steps a) through c) are all performed in a single container.

2. The method of claim 1, wherein the quantification in a) for viral capsid and in c) for viral DNA is determined from a reference standard curve, or, wherein, the quantification in a) for viral capsid and in c) for viral DNA is determined by digital PCR.

3. The method of claim 2, wherein the viral preparation is selected from the group consisting of parvovirus, adeno-associated virus (AAV), adenovirus, herpesvirus, poxvirus, baculovirus, and combinations thereof.

4. The method of claim 1, wherein the heating of step b) is at least at 80° C.

5. The method of claim 1, wherein the heating of step b) is up to 100° C.

6. The method of claim 1, wherein the method of quantifying the viral capsids and the viral DNA is done within about 4 hours.

7. The method of claim 1, wherein the viral preparation comprises one or more of full genome-containing virus particles, partial genome-containing virus particles, self-complementary genome-containing virus particles comprising a double stranded genome, and genome-free virus particles.

8. The method of claim 1, further comprising evaluating a percentage or ratio of full viral capsids versus empty viral capsids in the viral preparation.

9. The method of claim 8, wherein the percentage of full viral capsids is from about 1% to about 100%.

10. The method of claim 8, wherein the percentage of full viral capsids is from about 60% to about 100%.

11. A method of measuring the concentration of full AAV capsids in an AAV preparation, comprising:
    a) quantifying a total number of AAV capsids in the AAV preparation via an AAV-specific proximity ligation assay (PLA) assay;
    b) heating the AAV preparation to enable disassembly of the AAV capsids, and releasing the AAV DNA;
    c) quantifying the total amount of AAV DNA in the AAV preparation via an AAV DNA-specific quantitative PCR assay; and,
    d) evaluating a percentage of full AAV capsids versus empty AAV capsids in the AAV preparation by calculating the ratio of AAV DNA quantity to AAV capsid quantity, wherein the steps a) through c) are all performed in a single container.

12. The method of claim 11, wherein the quantification in a) for AAV capsids and in c) for AAV DNA is determined from a reference standard curve, or, wherein, the quantification in a) for AAV capsids and in c) for AAV DNA is determined by digital PCR.

13. The method of claim 11, wherein the PLA assay is capable of detecting one or more of thirteen serotypes of an AAV capsid antigen.

14. The method of claim 11, further comprising evaluating a percentage or ratio of full AAV capsids versus empty AAV capsids in the AAV preparation.

15. The method of claim 14, wherein the percentage of full AAV capsids is from about 1% to about 100%.

16. The method of claim 11, wherein the AAV capsids have an antigen that is selected from the group consisting of: AAV1, AAV2, AAV3, AAV4, AAV5, AAV6, AAV7, AAV8, AAV9, AAV10, AAV11, AAV12, AAV13, chimeric AAV, genetically engineered AAV, or chemically modified AAV.

17. The method of claim 11, wherein optionally, the AAV preparation is concentrated, and further wherein the preparation is administered at a specific dose to a subject in need thereof.

* * * * *